(12) United States Patent　(10) Patent No.: US 7,077,956 B2
Rovatti　(45) Date of Patent: Jul. 18, 2006

(54) DEVICE FOR PREPARING DIALYSATE FOR A DIALYSIS MACHINE

(75) Inventor: Paolo Rovatti, Finale Emilia (IT)

(73) Assignee: Gambro Lundia AB, Lund (SE)

( * ) Notice: Subject to any disclaimer, the term of this patent is extended or adjusted under 35 U.S.C. 154(b) by 334 days.

(21) Appl. No.: 10/479,608

(22) PCT Filed: May 6, 2002

(86) PCT No.: PCT/IB02/01611

§ 371 (c)(1), (2), (4) Date: Dec. 4, 2003

(87) PCT Pub. No.: WO02/098489

PCT Pub. Date: Dec. 12, 2002

(65) Prior Publication Data

US 2004/0217057 A1　Nov. 4, 2004

(30) Foreign Application Priority Data

Jun. 5, 2001　(IT)　............................ BO2001A0353

(51) Int. Cl.
*B01D 61/26*　(2006.01)
*B01F 15/00*　(2006.01)

(52) U.S. Cl. .................. 210/258; 210/85; 210/252; 210/254; 210/257.1; 210/321.71; 210/416.1; 422/261; 366/163.2

(58) Field of Classification Search ............... 210/252, 210/254, 257.1, 258, 321.71, 416.1, 647, 210/85; 422/256, 261; 366/131, 136, 159.1, 366/163.1, 163.2, 167.1
See application file for complete search history.

(56) References Cited

U.S. PATENT DOCUMENTS

| | | | | |
|---|---|---|---|---|
| 3,690,340 | A | * 9/1972 | Sipin | ............................ 137/93 |
| 4,202,760 | A | 5/1980 | Hall et al. | |
| 4,784,495 | A | * 11/1988 | Jonsson et al. | ........... 366/151.1 |
| 5,511,875 | A | * 4/1996 | Jonsson et al. | ............. 366/136 |
| 5,547,645 | A | * 8/1996 | Ego et al. | .................... 422/264 |
| 5,714,060 | A | 2/1998 | Feldsein et al. | |
| 5,972,223 | A | * 10/1999 | Jonsson et al. | ............. 210/647 |
| 6,308,721 | B1 | * 10/2001 | Bock et al. | ............. 134/166 R |
| 6,428,706 | B1 | * 8/2002 | Rosenqvist et al. | ......... 210/646 |
| 6,440,311 | B1 | * 8/2002 | Rosenqvist et al. | ......... 210/744 |
| 6,787,032 | B1 | * 9/2004 | Kurome et al. | ........... 210/257.1 |
| 6,884,441 | B1 | * 4/2005 | Pippert et al. | ............. 424/678 |

FOREIGN PATENT DOCUMENTS

| | | |
|---|---|---|
| DE | 198 52 982 C1 | 3/2000 |
| DE | 199 24 513 C1 | 8/2000 |
| EP | 0 469 487 A1 | 2/1992 |
| FR | 2 749 763 | 12/1997 |

* cited by examiner

*Primary Examiner*—John S. Kim
(74) *Attorney, Agent, or Firm*—Finnegan, Henderson, Farabow, Garrett & Dunner, L.L.P.

(57) ABSTRACT

A device for preparing dialysate for a dialysis machine is provided with a cartridge (9) containing salts (S), a first line (6) for supplying purified water to the cartridge (9) to form a saturated solution in the said cartridge (9), a second lin (7) for supplying the said saturated solution from the cartridge (9) to the first line (6) and for mixing the saturated solution with the purified water and forming the dialysate, and a discharge line (18) for discharging the said saturated solution from the second line (7) and from the said cartridge (9) at the end of the dialysis treatment.

8 Claims, 1 Drawing Sheet

DEVICE FOR PREPARING DIALYSATE FOR A DIALYSIS MACHINE

The present invention relates to a device for preparing a solution for a dialysis machine.

A dialysis machine of the known type generally comprises a blood circulation circuit, a dialysate circulation circuit and a filter, which comprises a dialysate compartment, a blood compartment and a semi-permeable membrane to separate the dialysate compartment from the blood compartment. The dialysate compartment is connected to the dialysate circuit, and the blood compartment is connected to the blood circuit, in such a way that the blood to be treated and the dialysate, generally flowing in opposite directions, pass through the blood compartment and the dialysate compartment respectively during the dialysis treatment.

During the dialysis treatment, unwanted particles contained in the blood migrate from the blood compartment to the dialysate compartment through the semi-permeable membrane both by diffusion and by convection, as a result of the passage of some of the liquid contained in the blood towards the dialysate compartment. Thus the patient will have lost some weight by the end of the dialysis treatment.

The dialysate is a solution of salts in purified water, and is supplied to the dialysate circuit by a device for preparing the solution, which will be referred to more simply as a "device" in the following description. The device comprises a cartridge of salts or solute, a first line for supplying the purified water to the cartridge, in which the purified water forms a saturated solution with the salts, and a second line for supplying the saturated solution from the cartridge to the first line in which it is mixed with the purified water to form a solution having a specified concentration of salts, this solution being the dialysate. The device described above supplies the dialysate continuously and in the quantities and concentrations specified for the aforesaid circuit throughout the dialysis treatment. When the dialysis treatment ends, the cartridge remains full of saturated solution mixed with the solute. The cartridge is frequently removed from the device at the end of the dialysis treatment, and is sometimes replaced with a cartridge containing different types of salts. The fact that the cartridge is full of saturated solution places considerable restrictions on the handling of the cartridge.

The object of the present invention is to produce a device for preparing dialysate for a dialysis machine which limits the drawbacks of the known devices.

According to the present invention, a device for preparing dialysate for a dialysis machine is produced, the device comprising a cartridge containing salts, a first line for supplying a solvent to the said cartridge to form a saturated solution in the said cartridge, a second line for supplying the said saturated solution from the cartridge to the first line and for mixing the saturated solution with the solvent to provide a dialysate having a specified concentration; the device being characterized in that it comprises a discharge line for discharging the said saturated solution from the second line and from the said cartridge at the end of the dialysis treatment.

The device for preparing dialysate, being provided with a discharge line, makes it possible to discharge the saturated solution from the cartridge and from the second line before the cartridge is removed, and prevents the leakage of saturated solution from the cartridge during the removal of the cartridge.

In a particularly convenient embodiment of the present invention, the device comprises suction means connected to the said discharge line.

Thus a particularly efficient emptying is achieved.

In a further embodiment of the present invention, the suction means comprise a Venturi tube acting as an ejector.

Thus the suction of the saturated solution is carried out in a particularly economical way.

BRIEF DESCRIPTION OF THE DRAWING

To enable the present invention to be understood more clearly, a preferred embodiment will now be described, purely by way of example and without restrictive intent, with reference to FIG. 1, which is a schematic view, with parts removed for clarity, of a dialysis machine provided with a device for preparing a solution produced according to the present invention.

DETAILED DESCRIPTION

Figure 1:
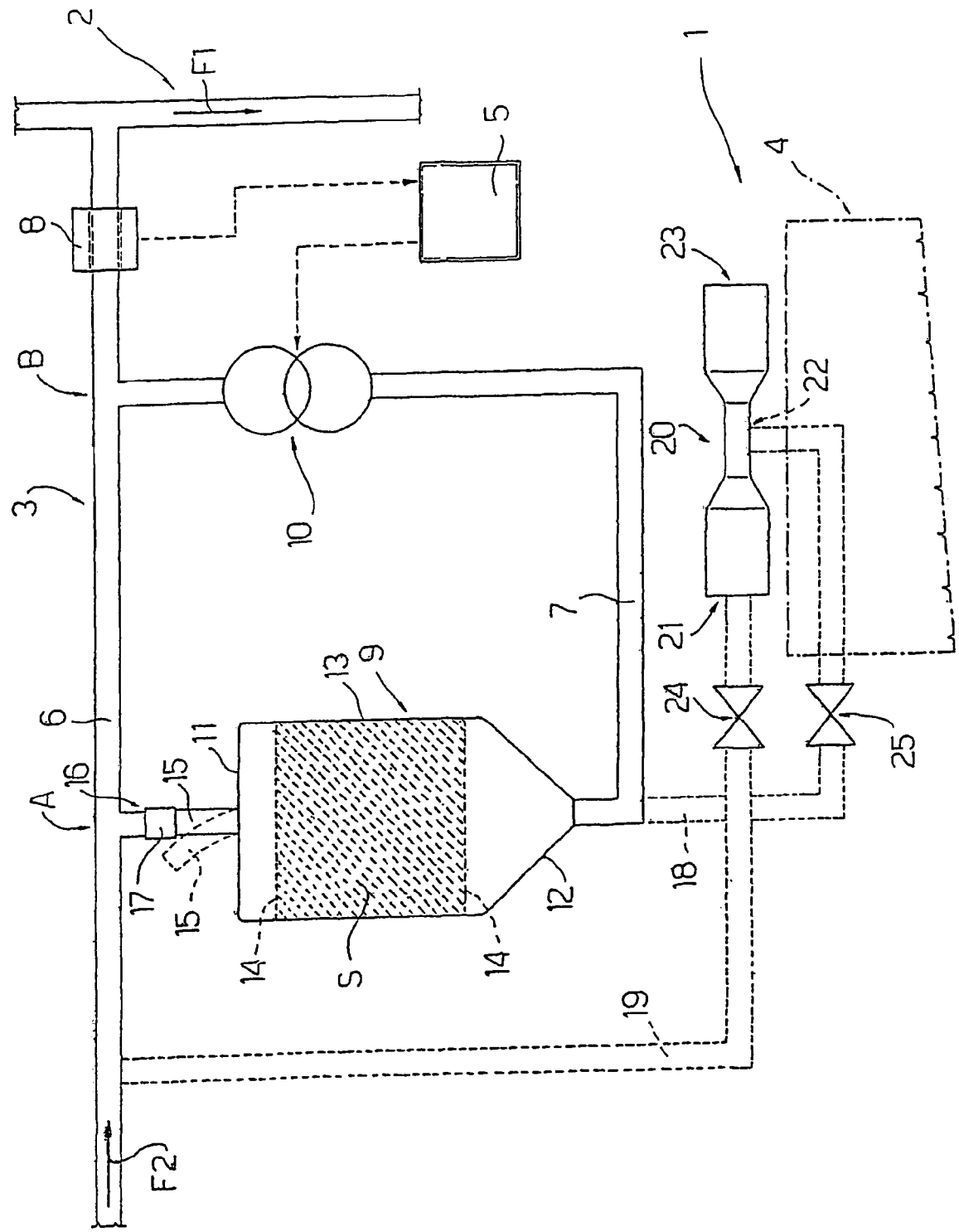

In the attached FIGURE, the number 1 indicates as a whole a dialysis machine, which comprises a dialysate circuit 2, a device 3 for supplying the dialysate to the circuit 2, a machine casing 4 (shown in chained lines in the attached FIGURE), and a control unit 5. The dialysate is a solution of salts, which is generally variable in concentration during the dialysis treatment according to a predetermined law, and which is conveyed in the direction of flow F1.

The device 3 comprises a line 6 connected at one end to a purifier (not illustrated) which supplies purified water, and at the opposite end to the circuit 2, a by-pass line 7 shown in solid lines in the attached FIGURE, and a conductivity cell 8. The device 3 also comprises a container or cartridge 9 and a pump 10 placed in sequence along the line 7. The purified water is conveyed along the line 6 in the direction of flow F1 and the by-pass line 7 can extract a certain quantity of the purified water at a point A from the line 6 and can inject the extracted quantity of purified water at a point B (down-line from the point A in the direction of flow F1) along the line 6 when this extracted quantity has been mixed with salts to form a saturated solution.

The cartridge 9 is filled with salts S in the granular state and comprises a top wall 11, a bottom wall 12, a side wall 13 and two filters 14 located inside the container 8 and forming, together with the side wall 13, a compartment which is occupied by the salts S. The filters 14 are permeable by the fluids and can retain the salts S. The cartridge 9 forms an integral part of the by-pass, since the liquid drawn from the line 6 passes through it, and it comprises a tube 15, which extends from the top wall 11 and can be selectively plugged into a branch 16 of the line 6, while the bottom wall 12 is connected to the by-pass line 7. In the attached FIGURE, the tube 15 is shown in broken lines in a disconnected position, and in solid lines in a position of connection to the line 6. The branch 16 is provided with a connector 17, which also acts as a valve, in that the connector 17 permits the passage of water when the tube 15 is plugged in and prevents the passage of water when the tube 15 is disconnected. The pump 10 is a positive displacement pump whose speed is variable so that a variable flow Q can be provided.

The device 3 also comprises two discharge lines 18 and 19 and a Venturi tube 20, connected to the machine casing 4. The Venturi tube 20 acts as an ejector, and as such has main inlet 21, a secondary inlet 22 located in the central constriction of the Venturi tube 20, and an outlet 23. The line 18 connects the by-pass line 7 to the secondary inlet 22 of the Venturi tube 20. The line 18 is plugged into the line 7 between the container 9 and the pump 10, and has a flow shut-off valve 25, which is normally closed during the dialysis treatment.

The line 19 connects the line 6 to the main inlet 21 of the Venturi tube 20. The line 19 is plugged into the line 6 up-line (with reference to the direction of flow F2 of the purified water) from the branch 16 and has a flow shut-off valve 24.

The control unit 5 is connected to the conductivity cell 8, which measures in a known way the concentration of the solution which passes through the cell 8 and to the pump 10 to regulate the speed and flow rate Q of the pump 10. The measurement of the concentration of the solution is based on the fact that the conductivity of the solution and the concentration of salts in the solution are related to each other by a known law. Therefore, in the field of application of dialysis machines, each reference to the conductivity of the solution is equivalent to a reference to the concentration of the solution. The control unit 5 measures the conductivity and compares the measured value with a set value and varies the flow rate of the pump 10 as a function of the difference between the set value and the measured value.

In use, during the dialysis treatment, the valves 24 and 25 are closed, the tube 15 is plugged into the branch, and the device 3 supplies the dialysate to the circuit 2. The dialysate is a solution of salts having a specified concentration, which is predetermined for each patient and varies during the dialysis treatment. The device 1 can therefore vary the concentration of the dialysate by regulating the pump 10. The purified water is conveyed along the line 6, and, at the branch 16, some of it continues along the line 6 and some is conveyed through the cartridge 10 where it comes into contact with the salts S and forms a saturated solution, which in turn is injected by means of the pump 10 into the line 6 at the point B. The saturated solution and the purified water are mixed to form a solution of salts having a concentration below the saturation level, in other words an unsaturated solution. The concentration of the unsaturated solution is measured by the conductivity cell 8 and, as described above, the control unit 5 operates the pump 10 according to the difference between the concentration of the unsaturated solution and the set concentration. For example, when the control unit 5 finds that the concentration of the unsaturated solution is lower than the set concentration, the control unit 5 increases the flow rate Q of the pump 10, in other words the flow rate Q of the saturated solution. The increase of the flow rate Q causes a decrease in the flow rate of purified water at the point B. Consequently, the concentration of the unsaturated solution instantaneously rises. Conversely, when the control unit 5 finds that the concentration of the unsaturated solution is greater than the set concentration, the control unit 5 decreases the flow rate Q of the pump 10, thus automatically lowering the concentration of the unsaturated solution. Generally, the set concentration varies between a maximum value at the start of the dialysis treatment and a minimum value at the end of the dialysis treatment. A threshold value which varies with time is therefore set in the control unit 5.

At the end of the dialysis treatment, the pump 10 is stopped and the tube 15 is disconnected from the branch 16. At this stage, the lines 6 and 7 and the cartridge 9 are occupied by purified water and saturated solution. The valves 24 and 25 are then opened, and the purified water flows through the line 19 and the Venturi tube 20, while the saturated solution flows through the tube 18 and the Venturi tube 20. In practice, the operation of the Venturi tube 20 as an ejector causes the purified water conveyed between the main inlet 21 and the outlet 23 to act as the primary fluid and causes the solution conveyed between the secondary inlet 22 and the outlet 23 to act as the secondary fluid, which is sucked in by the pressure drop created by the primary fluid. Thus, while the saturated solution contained in the circuit 6 is discharged, the saturated solution contained in the cartridge 9 is also efficiently sucked out in a particularly economical way, since there is no need to fit suction devices provided with their own drive systems, the flow of purified water being sufficient for the purpose.

The invention claimed is:

1. A device for preparing a dialysis solution comprising:
   a first line having an inlet end connected to a supply of a solvent, an outlet end connected to a dialysate circuit, a first extraction point, a second extraction point located between the inlet end and the first extraction point, and an injection point;
   a cartridge containing at least one salt and having an inlet connected to the first extraction point and an outlet connected to the injection point;
   a branch connecting said cartridge inlet to the first extraction point for supplying the solvent to the cartridge and for forming a saturated solution of at least one salt and solvent;
   a second line connecting said cartridge outlet to said injection point for supplying said saturated solution from the cartridge to the first line and for mixing the saturated solution with the solvent;
   a pump located in said second line for circulating said saturated solution;
   a discharge line connected to the second line between the cartridge and the pump for discharging said saturated solution from the second line and from the cartridge;
   a Venturi tube connected to said discharge line for sucking said saturated solution from the second line and from the cartridge, said Venturi tube comprising a primary inlet, a primary outlet, and a secondary inlet, said discharge line being connected to said secondary inlet; and
   a supply line connected to said primary inlet and to said second extraction point for supplying a flow of solvent to the Venturi tube and for creating a pressure drop at the secondary inlet.

2. A device according to claim 1, wherein the supply line is provided with a flow shut-off valve.

3. A device according to claim 1, further comprising a valve located in the discharge line to close the connection of the Venturi tube with the cartridge and the second line.

4. A device according to claim 1, wherein the cartridge comprises a tube extending from said cartridge inlet, said tube being selectively pluggable into said branch.

5. A device according to claim 1, further comprising means located in said branch for interrupting the flow of solvent from the first extraction point to the cartridge.

6. A device according to claim 5, wherein said interrupting means comprises a valvular connection.

7. A device according to claim 1, further comprising a conductivity cell located in the first line between the injection point and the outlet end for measuring the concentration of a solution formed by mixing said saturated solution with said solvent.

8. A device according to claim 7, wherein the injection point is located between the conductivity cell and the first extraction point.

* * * * *

UNITED STATES PATENT AND TRADEMARK OFFICE
CERTIFICATE OF CORRECTION

PATENT NO. : 7,077,956  Page 1 of 1
APPLICATION NO. : 10/479608
DATED : July 18, 2006
INVENTOR(S) : Paolo Rovatti It is certified that error appears in the above-identified patent and that said Letters Patent is hereby corrected as shown below:

On the title page, item (57), line 4, "lin" should read --line--.

Signed and Sealed this

Twelfth Day of September, 2006

JON W. DUDAS
*Director of the United States Patent and Trademark Office*